United States Patent [19]

Linscheid et al.

[11] Patent Number: 5,405,400
[45] Date of Patent: Apr. 11, 1995

[54] JOINT PROSTHESIS ENABLING ROTARY CIRCUMDUCTION

[75] Inventors: Ronald L. Linscheid, Rochester; Albert L. Lippincott, III, Prior Lake, both of Minn.

[73] Assignees: Orthomet, Inc., Minneapolis; Mayo Foundation, Rochester, both of Minn.

[21] Appl. No.: 132,296

[22] Filed: Oct. 5, 1993

[51] Int. Cl.⁶ .................................................. A61F 2/42
[52] U.S. Cl. ........................................ 623/21; 623/18
[58] Field of Search .................................... 623/18, 21

[56] References Cited

U.S. PATENT DOCUMENTS

| | | |
|---|---|---|
| 2,422,302 | 6/1947 | Horn . |
| 3,462,765 | 8/1969 | Swanson . |
| 3,466,669 | 9/1969 | Flatt . |
| 3,506,982 | 4/1970 | Steffee . |
| 3,593,342 | 7/1971 | Niebauer et al. . |
| 3,638,243 | 2/1972 | Campbell, Jr. et al. . |
| 3,651,521 | 3/1972 | Devas . |
| 3,739,403 | 6/1973 | Nicolle . |
| 3,760,427 | 9/1973 | Schultz . |
| 3,772,709 | 11/1973 | Swanson . |
| 3,805,302 | 4/1974 | Mathys . |
| 3,818,513 | 6/1974 | Pillet . |
| 3,824,631 | 7/1974 | Burstein et al. . |
| 3,875,594 | 4/1975 | Swanson . |
| 3,886,600 | 6/1975 | Kahn et al. . |
| 3,924,276 | 12/1975 | Eaton . |
| 3,946,445 | 10/1976 | Bentley et al. . |
| 3,986,212 | 10/1976 | Sauer . |
| 3,990,116 | 11/1976 | Fixel et al. . |
| 3,990,118 | 11/1976 | Strickland et al. . |
| 3,991,425 | 11/1976 | Martin et al. . |
| 3,992,726 | 11/1976 | Freeman et al. . |
| 4,011,603 | 3/1977 | Steffee . |
| 4,021,864 | 5/1977 | Waugh ........................... 623/21 X |
| 4,059,854 | 11/1977 | Laure . |
| 4,106,128 | 8/1978 | Greenwald et al. . |
| 4,158,893 | 6/1979 | Swanson . |
| 4,194,250 | 3/1980 | Walker . |
| 4,204,284 | 5/1980 | Koeneman . |
| 4,213,208 | 7/1980 | Marne . |
| 4,231,121 | 11/1980 | Lewis . |
| 4,242,759 | 1/1981 | White ........................... 623/21 X |
| 4,246,662 | 1/1981 | Pastrick . |
| 4,276,660 | 7/1981 | Laure . |
| 4,304,011 | 12/1981 | Whelan, III . |
| 4,313,232 | 2/1982 | Habal et al. . |
| 4,352,212 | 10/1982 | Greene et al. . |
| 4,367,562 | 1/1983 | Gauthier . |
| 4,375,703 | 3/1983 | Evans et al. . |
| 4,516,569 | 5/1985 | Evans et al. . |
| 4,634,445 | 1/1987 | Helal . |
| 4,685,919 | 8/1987 | Niwa . |
| 4,759,768 | 7/1988 | Hermann et al. . |
| 4,911,719 | 3/1990 | Merle . |
| 4,944,758 | 7/1990 | Bekki et al. . |
| 4,955,916 | 9/1990 | Carignan et al. ........................... 623/23 X |
| 5,007,932 | 4/1991 | Bekki et al. . |
| 5,047,059 | 9/1991 | Saffar . |
| 5,092,896 | 2/1992 | Meuli et al. . |
| 5,133,761 | 7/1992 | Krouskop . |

FOREIGN PATENT DOCUMENTS

| | | | |
|---|---|---|---|
| 2669215 | 5/1992 | France ........................... | 623/21 |
| 1582974 | 1/1981 | United Kingdom ........................... | 623/21 |
| 9300053 | 1/1993 | WIPO . | |

Primary Examiner—David Isabella
Assistant Examiner—Laura Fossum
Attorney, Agent, or Firm—Frederikson & Byron

[57] ABSTRACT

A joint prosthesis is provided for replacing a joint between two bones in which one bone is normally permitted a substantial degree of rotary circumduction with respect to a second bone. A first member of the prosthesis is provided with a coupling portion enabling it to be attached to the elongated bone and includes a head having a generally saddle-shaped articulating surface facing away from the stem. The second member similarly has a connector adapted to connect the second member to the second bone, and has a head provided with a saddle-shaped articulating surface configured and sized to articulate with the saddle-shaped surface of the first member to enable one of the long bones to move in rotary circumduction with respect to the other. The saddle-shaped surfaces preferably are substantially congruent in shape.

14 Claims, 5 Drawing Sheets

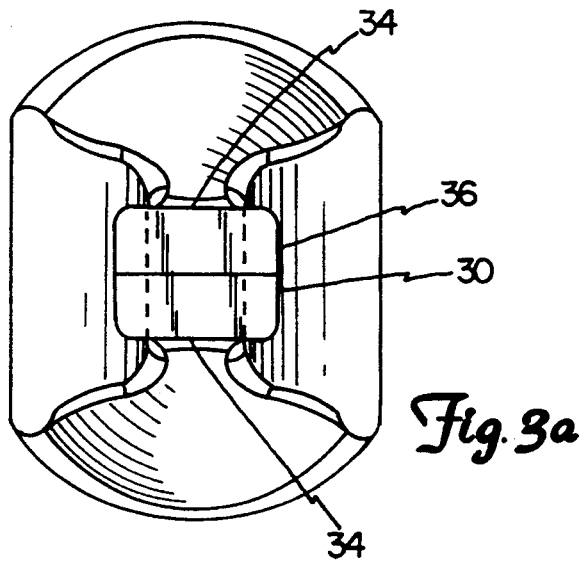
Fig. 3a
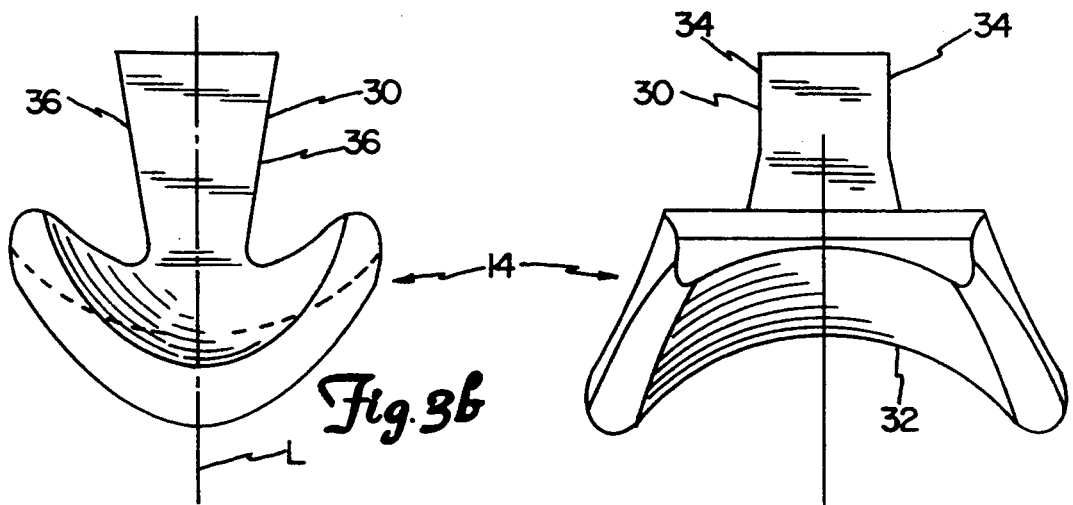
Fig. 3b
Fig. 3d
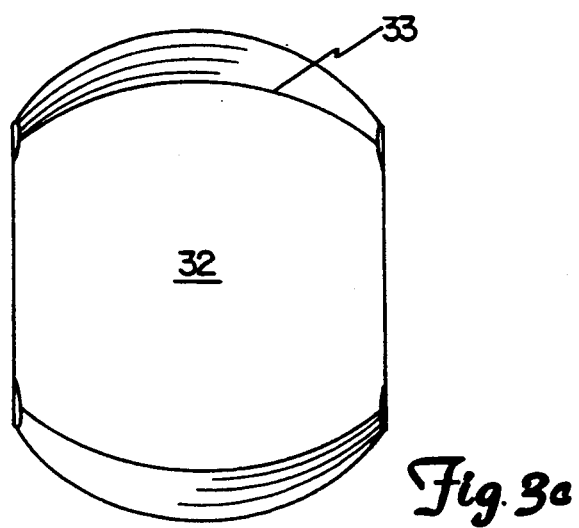
Fig. 3c

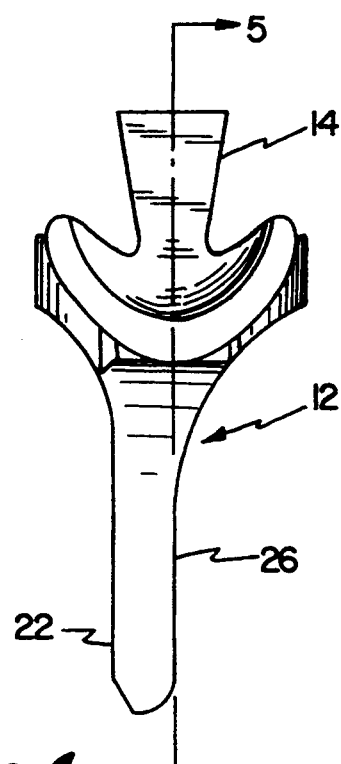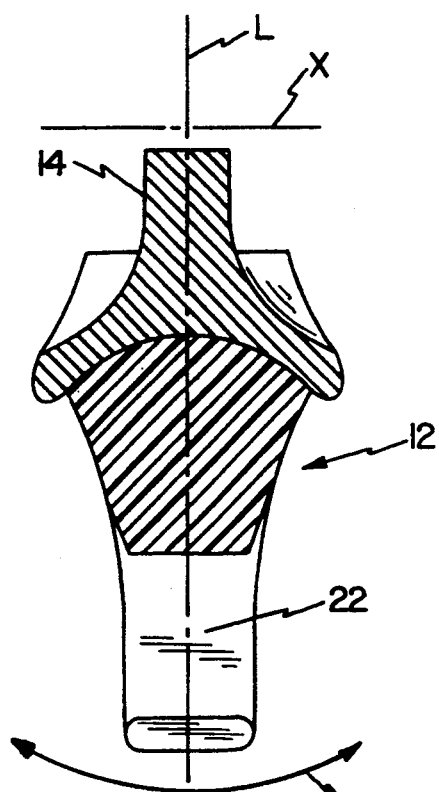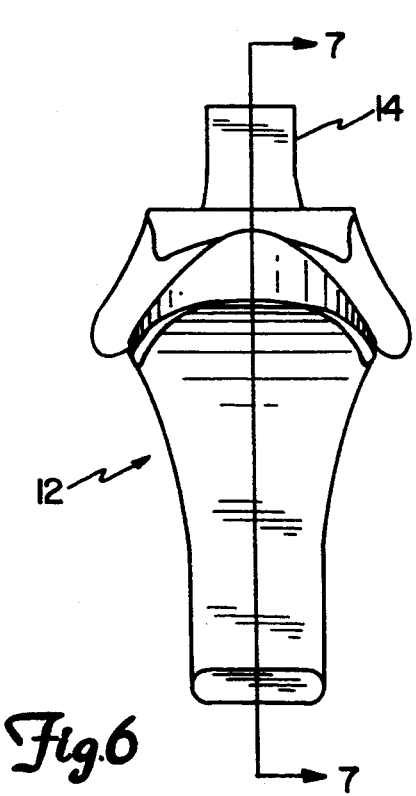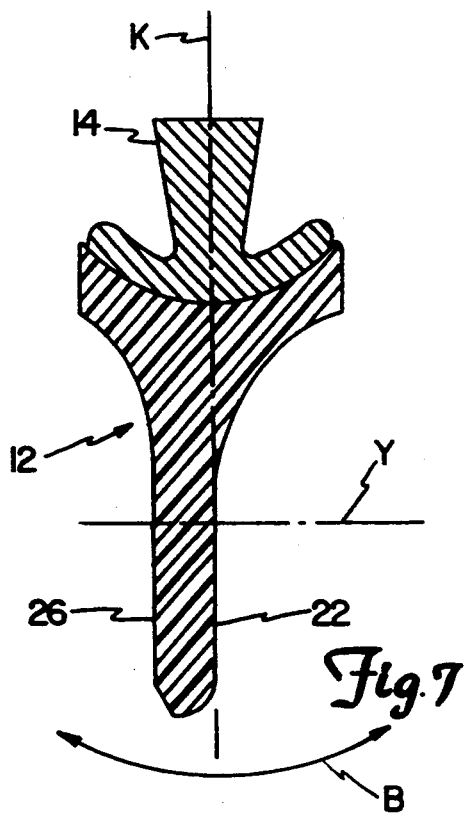

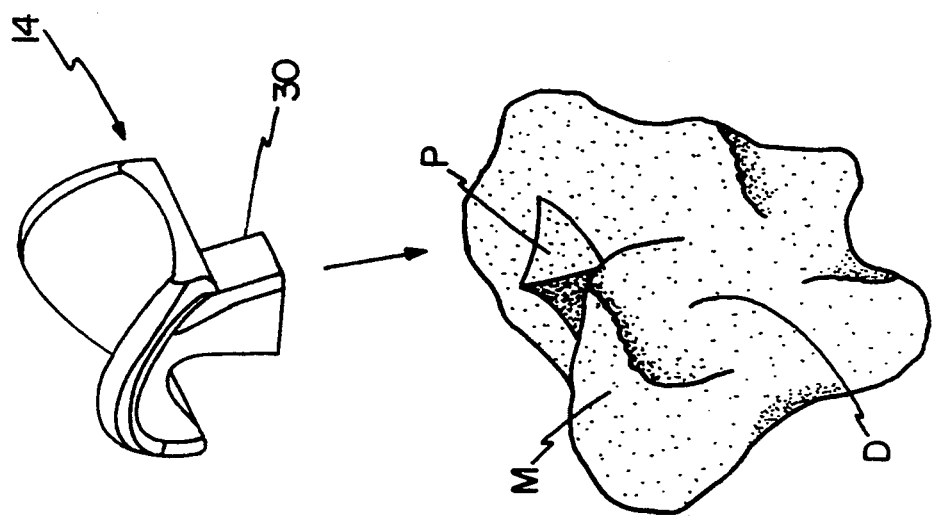
Fig. 9
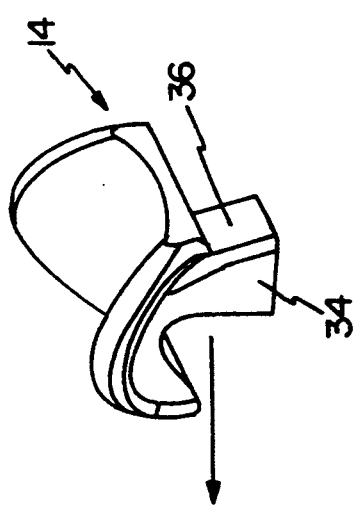
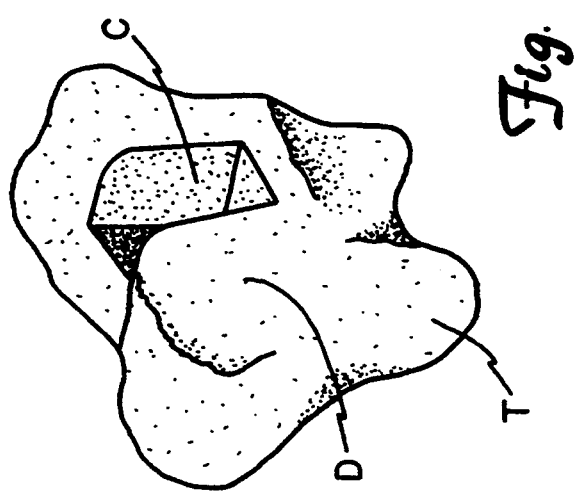
Fig. 8

JOINT PROSTHESIS ENABLING ROTARY CIRCUMDUCTION

BACKGROUND OF THE INVENTION

The invention relates to joint prosthesis particularly adapted for replacing a joint, such as the joint between the first metacarpal and the trapezium of the human hand, in which one elongated bone (e.g., the first metacarpal) is normally permitted a substantial degree of rotary circumduction with respect to a second bone (e.g., the trapezium), without substantial rotation of the elongated bone about its axis.

Various efforts have been made to design an appropriate joint prostheses to replace damaged or diseased first metacarpal-trapezium joints. Carigman et al., U.S. Pat. No. 4,955,916 and Horn, U.S. Pat. No. 2,422,302, for example, disclose ball and socket joint designs, whereas Eaton, U.S. Pat. No. 3,924,276 discloses a trapezium prosthesis, the use of which employs a segment of the flexor carpi radialis tendon.

SUMMARY OF THE INVENTION

The present invention provides a joint prosthesis particularly suited for use in replacing the joint between an elongated first bone such as the first metacarpal bone and a second bone such as the trapezium with respect to which the first bone should be permitted a substantial degree of rotary circumduction without substantial rotation about its longitudinal axis. The prosthesis includes a first member having a coupling portion enabling attachment of the first member to an elongated bone and a second member having a connector adapted for connection of the second member to a second bone. The first and second members have respective articulating saddle-shaped surfaces configured and sized to articulate with each other to enable the long bone to move in rotary circumduction with respect to the other bone. Preferably, the saddle-shaped articulating surfaces are substantially congruent in shape to maintain mutual substantially surface-to-surface contact over the range of normal articular movement between the bones. The articulating surfaces preferably have approximately the same area so that when they are aligned, each articulating surface substantially completely overlaps the other.

In a preferred embodiment, the prosthesis is adapted in size and shape to replace the articulating joint between the trapezium and the first metacarpal. The first member has a stem that is asymmetric with respect to its articulating surface, the stem being received in the first metacarpal bone in a preferred orientation. That orientation positions the saddle-shaped articulating surface of the first member with respect to that of the second member such that the pivot axis for adduction/abduction of the first metacarpal is proximal of the respective articulating surfaces, and the pivot axis for dorsal/volar movement of the first metacarpal is distal of the articulating surfaces.

Articulating portions of the first and second members each have supporting surfaces that confront surgically prepared surfaces of the bones to which they are to be attached. To aid in reducing joint volume, the supporting surface of the articulating portion of the second member may be recessed to receive the surgically prepared surface of the second bone. The "elongated bone" may particularly be the first metacarpal which normally articulates with the trapezium. This joint affords the first metacarpal a substantial degree of rotary circumduction in which the first metacarpal may be rotated about the joint to sweep out a roughly conical shape, the cone having a included angle of at least about 15° and ranging generally between about 15° and 30°.

BRIEF DESCRIPTION OF THE DRAWING

FIGS. 3A, 3B, 3C, and 3D are orthographic views of a second member of a prosthesis of the invention FIG. 4 is a plan view of the articulating members shown in FIGS. 3A–3D and 2A–2D;

FIG. 5 is a cross sectional view taken along line 5—5 of FIG. 4;

FIG. 6 is a plan view of the prosthesis shown in FIG. 4, taken from the right hand side of FIG. 4;

FIG. 7 is a cross sectional view taken along line 7—7 of FIG. 6;

FIG. 8 is a perspective view showing a step in the implantation of the member shown in FIGS. 3A–3D; and FIG. 9 is a perspective view showing an alternate step in implantation of the member shown in FIGS. 3A–3D.

DETAILED DESCRIPTION OF THE PREFERRED EMBODIMENT

For ease of understanding, the prosthesis of the invention will be described in terms of the first metacarpal/trapezium joint.

The first member of the prosthesis has (as implanted) distal and proximal ends, the distal end comprising an elongated stem that is appropriately sized and shaped to fit within the surgically exposed marrow recess in the proximal end portion of the first metacarpal. Proximally, the first member includes an enlarged head provided with a proximally-facing saddle-shaped articulation surface. The stem may be offset slightly so as to provide a slightly convex aspect to the volar surface of the first metacarpal bone.

The second member, which is to be carried by the trapezium, has a proximally extending stem for reception within the trapezium and an enlarged head bearing a distally facing saddle shaped articulating surface that is substantially congruent to the saddle-shaped surface of the first member. It is the saddle shaped articulating surfaces that enable the first metacarpal to enjoy a substantial degree of rotary circumduction with respect to the trapezium without permitting substantial rotation of the first metacarpal about its axis. Substantially perfect congruency between the saddle-shaped surfaces—so that they fit together in broad surface-to-surface contact—permits substantially no rotation of the first metacarpal about its axis without concurrent axial movement of that bone as the saddle-shaped surfaces are rotated (and thus are separated) from each other. If desired, the respective saddle-shaped articulating surfaces of the first and second members may be of different sizes or of different shapes, or both, to enable varying degrees of respective rotational movement between the first metacarpal and the trapezium. In particular, one of the saddle-shaped surfaces may be more tightly or severly curved than the other, although they may substantially overlap each other.

Figure 1:
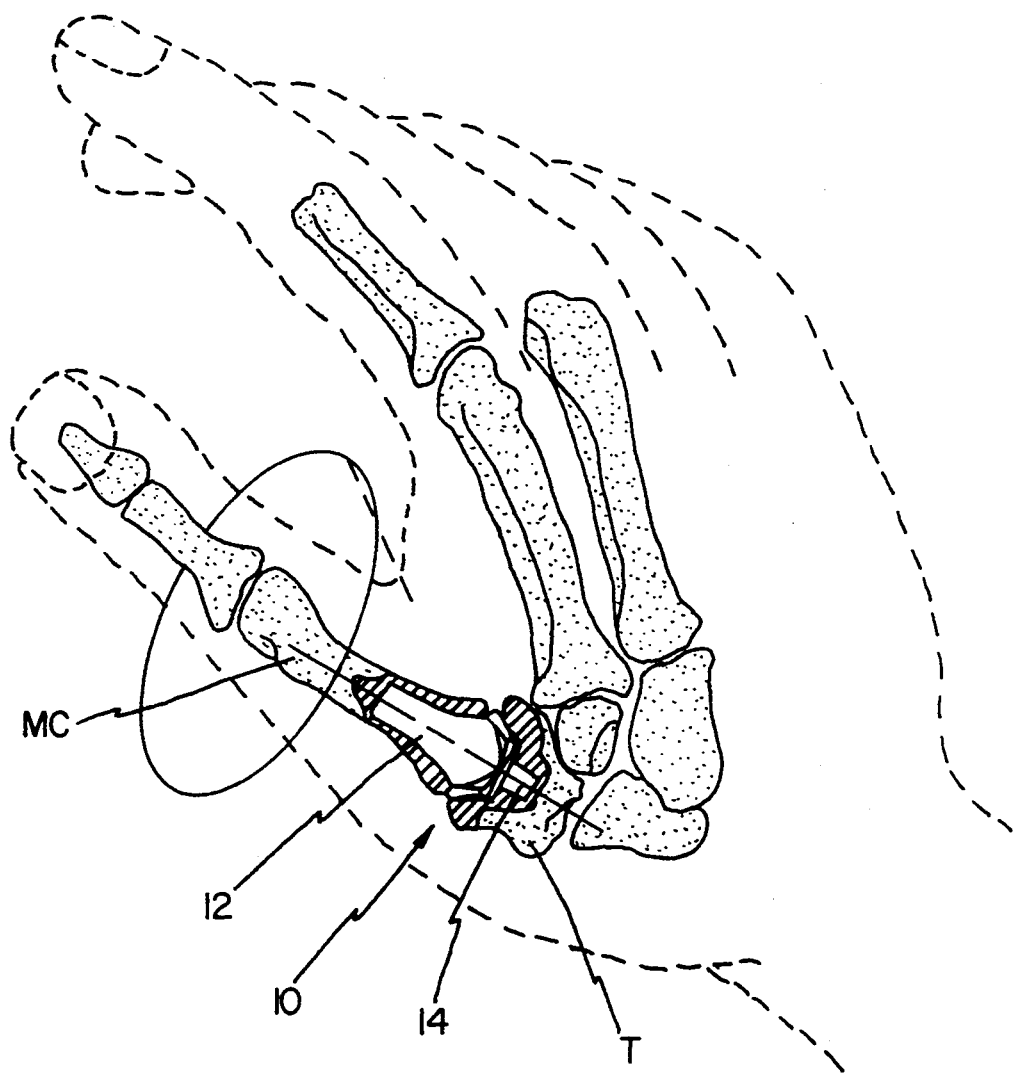
FIG. 1 is a view of bones of the hand and, wrist and within which has been implanted a prosthesis of the invention, the hand being shown in phantom lines.

Referring first to FIG. 1, the trapezium is designated "T" and the first metacarpal that articulates with the trapezium is designated "MC". The first metacarpal and trapezium are shown broken away adjacent their points of articulation, exposing respective first and second members 12, 14 of a prosthesis 10 of the invention.

Referring now to FIGS. 2A-2D, a first member 12 is shown in orthographic views as having an elongated, somewhat flattened stem 16 and an enlarged proximal head 18, the head having a proximally presented saddle-shaped articulating surface 20. The surface 20 may be considered a hyperbolic paraboloid. In a preferred embodiment, all points on the articulating surface 20 can be viewed from a concave aspect as being formed upon a radius "r".

Figure 2A:
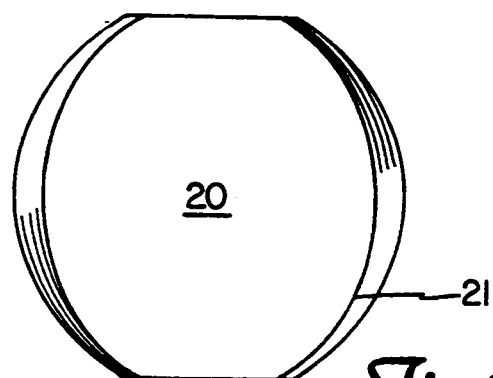
FIGS. 2A, 2B, 2C, and 2D are orthographic views of a first member of a prosthesis of the invention.
Figure 2B:
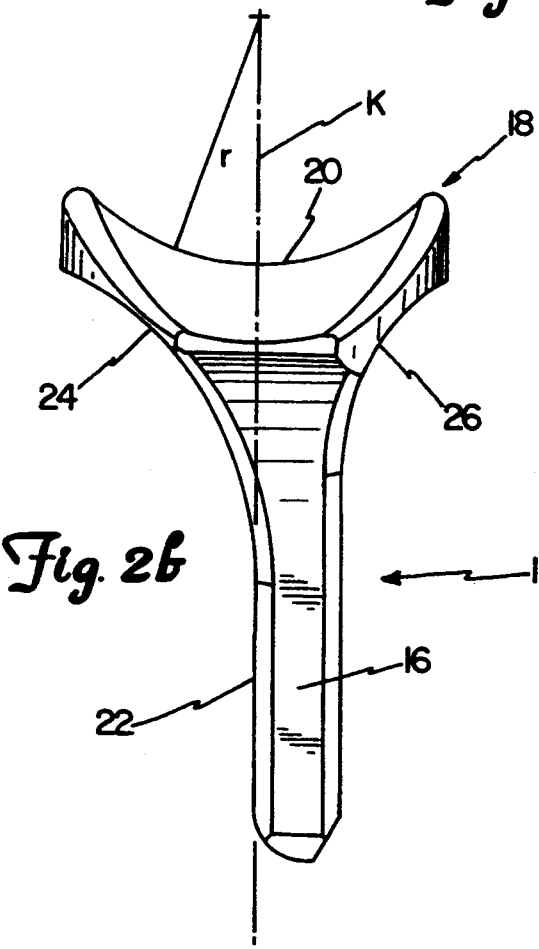

Stem portion 16 of the first member 12 shown in FIGS. 2A-2D is asymmetrical when viewed from the lateral aspect as in FIG. 2B with respect to the axis "K" of the hyperbolic paraboloid surface 20. The volar surface 22 of the stem is gently rounded at its proximal end 24, whereas the dorsal surface 26 is more tightly rounded at its proximal end. The stem is offset toward its dorsal surface, as shown best in FIG. 2B, so as to match more exactly the shape of the proximal end of the first metacarpal, the stem 16 being snugly received within the surgically exposed bone marrow cavity of the first metacarpal. As can be seen best from FIG. 2A, the saddle-shaped surface 20 presents a generally circular "footprint" or peripheral border 21 when viewed from the proximal end.

FIGS. 3A-3D show a second member 14 of the prosthesis adapted for attachment to the trapezium. This member includes a stem 30 for reception within a recess surgically prepared in the trapezium, and a saddle-shaped articular surface 32 adapted to articulate with the surface 20 of the member shown in FIGS. 2A-2D. The surface 32 is substantially congruent to the surface 20, and desirably is essentially perfectly congruent to the surface 20. As with the surface 20, the saddle-shaped surface 32 is generally of the shape of a hyperbolic paraboloid.

Figure 2D:
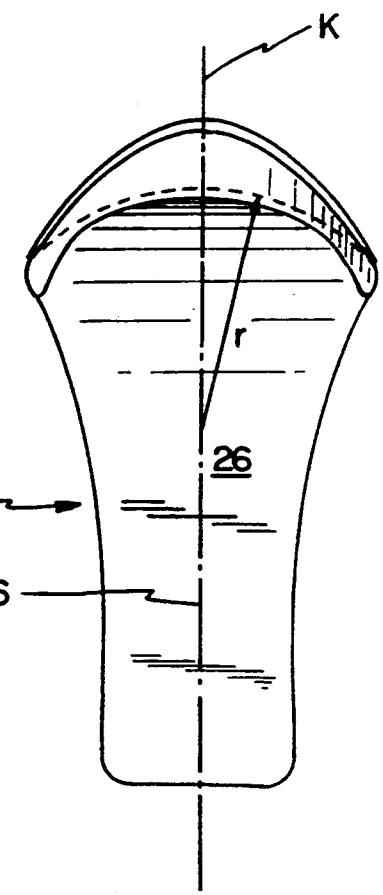

When viewed from the distal end as in FIG. 3C, the surface 32 presents a "footprint" 33 which is substantially the same as that presented by the surface 20 shown in FIG. 2A. When the surfaces 20 and 32 are in articulating contact with one another with their axes "K" and "L" generally aligned, the surfaces 32 and 20 cover one another over at least 70% of the larger saddle shaped area, preferably over at least 90% of that area so that at the limit of articulation, neither articulating surface extends beyond the other by more than about 10% of the surface area of the larger articulating surface. The stem 30 of member 14 is generally symmetric to the axis "L" of the hyperbolic paraboloid surface 32. Stem 30 has generally straight sides when viewed perpendicular to the volar or dorsal directions as in FIG. 3D, and these sides are designated generally as 34 in FIGS. 3A and 3D. When viewed from its proximal end, as in FIG. 3A, the stem will be seen to be generally rectangular in cross section, and the walls 36 of the stem that are generally at fight angles to the walls 34 diverge proximally to form a generally dovetail shape as shown best in FIG. 3B. The symmetry of the stem 30 with respect to the axis of the saddle-shaped articulating surface 32 enables the member 14 to be implanted in either the right hand or the left hand; that is, separate right and left hand prostheses are not required. Similarly, the stem 16 in FIG. 2D is symmetrical, when viewed from the volar or dorsal aspects, with respect to the axis K of the saddle-shaped articulating surface 20. Hence, this member also can be used for either the left or the right hand. Stems 16 and 30, of course, can be shaped as desired.

FIGS. 4-7 show articulation of the first and second members of the prosthesis. For ease of description, we here consider that when the prosthesis is implanted, the second member 14 that is attached to the trapezium is immovable, although in fact the trapezium is permitted some movement in normal motion of the hand for absorbing stress.

In the lateral views of FIGS. 4 and 7, articulation of the first metacarpal prosthesis member 12 purely in flexion and extension occurs about an axis X (FIG. 5) spaced proximally from the articulating surfaces. Purely flexion/extension movement is shown by the arrow B in FIG. 7. This movement of the thumb is the primary movement involved in grasping and releasing objects from the hand. In contrast, articulation of the member 12 in a near dorsal/volar direction (which may be described as abduction/adduction) takes place about an axis Y (FIG. 7) that is spaced distally from the articulating surfaces. Movement of the member 12 about this axis is shown by the arrow A in FIG. 5.

Movement of the thumb first metacarpal, of course, is rarely purely flexion/extension or abduction/adduction, but rather is a combination of such movements. For such compound movements, the pivot axis of the first member 12 is neither X (FIG. 5) nor Y (FIG. 7), but rather dynamically moves between the axes X and Y. The pivot axis will always lie along the axis K (FIG. 2B); that is, generally perpendicular to the articulating surface 20 of the first member. During compound movement of the joint, the axis of rotation will move along the axis K between points X and Y.

The orthopedic surgical procedures required to implant the prosthesis of the invention are straightforward. In one procedure, surgical access to the trapezium/first metacarpal joint is had dorsally, the surgeon preserving as much soft tissue as possible. The proximal end of the first metacarpal is exposed and surgically sculpted to receive the stem 16 and head portion 18 of the first metacarpal prosthesis member 12. This procedure may involve surgically enlarging the marrow cavity at the proximal end of the first metacarpal to appropriately receive the stem 16.

Figure 2C:
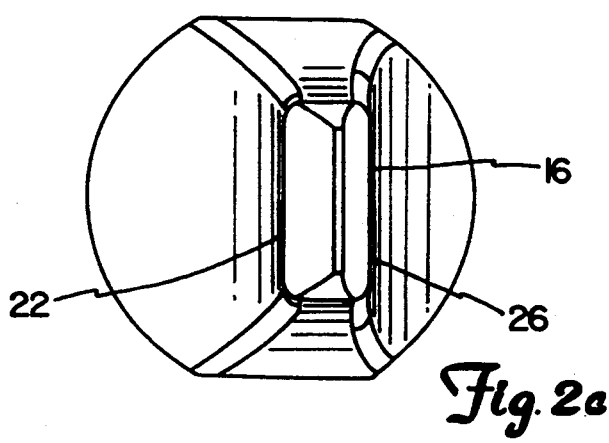

FIG. 8 shows a preferred procedure for attachment of the second member 14 to the trapezium T. The dorsal surface D of the trapezium is surgically exposed and a cavity "C" is made in the trapezium, the cavity extending from the dorsal surface toward the volar surface of the trapezium through slightly over half the thickness of the trapezium. The cavity C is open distally, as shown in FIG. 8. Sculpting of the distal surface of the trapezium is performed as needed to enable the proximally facing surfaces of the head of member 14 to snugly contact the distal surface of the trapezium. The parallel surfaces 34 of the stem are snugly received between the confronting walls of the cavity C. The relatively long stem of the first metacarpal member 12 is received within the marrow channel at the distal end of the first metacarpal. As shown in FIGS. 2B-2D, the stem 16 is substantially narrower in the dorsal-volar direction, and this matches to some extent the physiologic configuration of the first metacarpal marrow cavity. Thus, the first member 12 is received in the marrow cavity in only one orientation. Similarly, the stem 30 of member 14 is received in only one position in the trapezium, the saddle-shaped articulating surfaces of both members thus being positioned to articulate during normal movement of the first metacarpal. Bone cement is then used to hold both the first metacarpal portion 12 and the trapezium portion 14 in their respective bones. It is contemplated that it may be appropriate in some circumstances to cause the stems of the prosthesis members to fit fairly tightly in the bone cavities of the bones in which they are implanted, omitting the need for bone cement. In this event, the surfaces of the stems desirably are shaped or treated to encourage bone ongrowth or ingrowth, as by providing the stems with porous surfaces, by applying to the stems a cell adhesion promoter such as collagen or the like, etc.

The procedure depicted in FIG. 8, where entry into the trapezium is had from the dorsal surface of the trapezium, is preferred in that it does not require the trapezium to be moved with respect to the other carpal bones and results in maximum preservation of soft tissue. A second method of mounting the trapezium prosthetic member 14 is shown in FIG. 9. Here, the trapezium is surgically exposed by reflecting the first metacarpal base dorsally so that the distal surface M is presented. Using a burr or other sculpting tool, a cavity P is made through the distal surface of the trapezium of sufficient depth to receive the stem 30 of the second or trapezium member 14. Again, the distally presented surface M of the trapezium is suitably sculpted to receive snugly the proximally facing surfaces of the head of the trapezium member 14. Although this procedure has the drawback of requiring the first metacarpal base to be reflected dorsally to present the distal surface M of the trapezium, it has the benefit of not surgically interrupting the dorsal side wall D of the trapezium.

The forces imparted to the trapezium through the trapezium prosthetic member 14 are largely compressive in nature, and hence are transmitted from the undersurface of the trapezium member 14 to the distal surface of the trapezium. As the first metacarpal is articulated during a grasping or pinching movement, the surface 20 bears against the surface 32 with substantial sideways or laterally directed force, but this force again is transmitted to the trapezium largely through contact between the undersurface of the member 14 and the distal surface M of the trapezium. The stem 30 serves to hold the trapezium member 14 in place, but the stem 30 is not depended upon to bear loads.

Substantial bending moments as well as compressive forces are imparted to the first metacarpal member 12. The stem 16 of the first metacarpal member 12 thus bears a substantial bending load, and it is desired that the marrow cavity of the first metacarpal be carefully prepared to snugly receive the stem 16.

The first and second members may be made of any suitable, biologically acceptable joint replacement materials having adequate strength and wear characteristics including such well known materials as ultra high molecular weight polyethylene, cobalt-chrome alloys or titanium alloys. The members may be machined from solid pieces of such materials so as to avoid seams or weldments. In a preferred embodiment, the first member is machined from ultra high molecular weight polyethylene and the second member from cobalt/chrome alloy.

Referring again to FIG. 1, the prosthesis of the invention affords substantial rotary circumduction of the first metacarpal with respect to the trapezium. During such movement, the axis of the first metacarpal sweeps out a generally conical surface, but the cross section of that surface taken perpendicular to the axis of the first metacarpal is generally not circular but rather is elliptical in shape, with the first metacarpal having the greatest degree of freedom in the flexion/extension direction.

As mentioned above, the preferred embodiment employs articulating, saddle-shaped surfaces that are congruent to one another and which maintain substantial surface-to-surface contact between the articulating surfaces as the joint is articulated. Soft tissue constraints urge the two saddle-shaped surfaces together, thereby inhibiting rotation of the first metacarpal about its axis with respect to the trapezium. That is, rotation of the first metacarpal with respect to the trapezium would cause one saddle-shaped surface to twist with respect to the other, in turn causing the surfaces to separate from one another. However, some minor degree of rotation about its axis may be afforded the first metacarpal if desired, inasmuch as the first metacarpal in the normal hand structure twists slightly during grasping and ungrasping movements. To provide for twisting in this manner, the saddle-shaped surfaces may be formed on greater radii, thereby flattening to some extent these surfaces and reducing the degree of axial displacement of the first metacarpal in response to rotation about its longitudinal axis. Also, twisting motion of this type may be afforded by reducing the congruence of the saddle-shaped surfaces; that is, one surface may be formed on a radius that is somewhat greater than the other surface. In this modification, desirably the saddle-shaped surface of the trapezium member 14 is formed on a smaller radius than that of the first metacarpal portion, that is, the saddle-shaped surface of the trapezium member is more tightly curved.

The prosthesis thus described provides several unique features. The articulating members of the prosthesis can be implanted surgically with substantial preservation of soft tissue attachments. That is, ligamentous connections between the bones can largely be preserved. Second, bone integrity is conserved since only moderate sculpting is required of the articulating surfaces of either the first metacarpal or the trapezium. A particularly strong connection occurs between the first metacarpal bone and the stem of the first member of the prosthesis that fits in the marrow cavity of that bone. By offsetting the stem dorsally, the stem more readily matches the anatomy of the first metacarpal. Of perhaps greatest importance, however, is the fact that the prosthesis of the invention provides a full rotary circumduction of the metacarpal in a manner that mimics very closely the normal anatomy of the joint that is replaced.

While a preferred embodiment of the present invention has been described, it should be understood that various changes, adaptations and modifications may be made therein without departing from the spirit of the invention and the scope of the appended claims.

We claim:

1. A joint prosthesis for replacing a joint between an end of an elongated first bone and a second bone with respect to which the elongated bone normally is capable of a substantial degree of rotary circumduction, comprising a first member having a coupling portion enabling attachment of the first member to the elongated bone and a second member having a connector adapted for connection of the second member to the second bone, the first and second members having respective hyperbolic paraboloid articulating surfaces configured and sized to articulate with each other to enable the long bone to move in rotary circumduction with respect to the other bone.

2. The prosthesis of claim 1 wherein said articulating surfaces are substantially congruent in shape and maintain substantial surface-to-surface contact over a range of normal articular movement between the bones.

3. The prosthesis of claim 1 wherein said articulating surfaces are substantially congruent in shape and in area.

4. The joint prosthesis of claim 2 wherein said surfaces are sized such that within the range of normal articulation of the elongated bone, neither of the articulating surfaces extends beyond the other by more than about 10% of the surface area of the larger articulating surface.

5. The joint prosthesis of claim 1 wherein the coupling portion of the first member comprises a stem extending away from its articulating surface.

6. The prosthesis of claim 5 wherein the stem of the first member is asymmetric with respect to its articulating surface so that the stem is received in the long bone in a preferred orientation so as to provide a pivot axis for flexion/extension of the long bone that is proximal of the articulating surfaces and a pivot axis for adduction-abduction of the long bone that is distal of the articulating surfaces.

7. A joint prosthesis for replacing the first metacarpal-trapezium joint, comprising a first member having a first stem and a first head, the first head having a hyperbolic paraboloid articulating surface having an axis and facing away from the first stem and the first stem being displaced dorsally with respect to said axis of said articulating surface, said first stem being adapted for receipt within the marrow cavity of the proximal end of the first metacarpal, and a second member having a second stem and a second head having a hyperbolic paraboloid articulating surface facing away from the second stem, the second stem being sized and shaped for reception within the trapezium, the respective hyperbolic paraboloid surfaces nesting together in articulating contact when said members are received respectively within the first metacarpal and trapezium.

8. The joint prosthesis of claim 7 wherein the articulating surfaces are substantially congruent in shape.

9. The joint prosthesis of claim 7 wherein the articulating surfaces are substantially congruent in area.

10. The joint prosthesis of claim 7 wherein the articulating surfaces are substantially congruent in shape and in area.

11. The joint prosthesis of claim 7 wherein one of the hyperbolic paraboloid surfaces is more tightly curved that the other.

12. The joint prosthesis of claim 11 wherein said more tightly curved surface is the articulating surface of the second member.

13. The joint prosthesis of claim 7 wherein said surfaces are sized such that within the normal range of articulation of the elongated bone, neither of the articulating surfaces extends beyond the other by more than about 10% of the surface area of the larger of the articulating surfaces.

14. The prosthesis of claim 7 wherein said stem of the first member is asymmetric with respect to its articulating surface so that the stem is received in the first metacarpal in a preferred orientation such that the pivot axis for flexion/extension of the first metacarpal is proximal of the articulating surfaces and the pivot axis for abduction/adduction of the first metacarpal is distal of the articulating surfaces.

* * * * *